(12) United States Patent
Fine et al.

(10) Patent No.: US 7,772,367 B2
(45) Date of Patent: Aug. 10, 2010

(54) C-TERMINAL P53 PALINDROMIC PEPTIDE THAT INDUCES APOPTOSIS OF CELLS WITH ABERRANT P53 AND USES THEREOF

(75) Inventors: Robert L. Fine, Tenafly, NJ (US); Paul Brandt-Rauf, Scarsdale, NY (US); Yueha Mao, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 588 days.

(21) Appl. No.: 10/587,606

(22) PCT Filed: Jan. 27, 2005

(86) PCT No.: PCT/US2005/002543

§ 371 (c)(1),
(2), (4) Date: Nov. 13, 2006

(87) PCT Pub. No.: WO2005/074521

PCT Pub. Date: Aug. 18, 2005

(65) Prior Publication Data

US 2007/0173443 A1    Jul. 26, 2007

Related U.S. Application Data

(60) Provisional application No. 60/540,864, filed on Jan. 30, 2004.

(51) Int. Cl.
C07K 5/00 (2006.01)
C07K 14/00 (2006.01)
A61K 39/295 (2006.01)

(52) U.S. Cl. .................. 530/350; 424/184.1
(58) Field of Classification Search ........... None
See application file for complete search history.

(56) References Cited

U.S. PATENT DOCUMENTS 5,527,676 A * 6/1996 Vogelstein et al. ............. 435/6
5,545,727 A * 8/1996 Hoffman et al. ............ 536/23.4
5,721,340 A   2/1998 Halazonetis
5,770,377 A   6/1998 Picksley et al.
5,847,083 A   12/1998 Halazonetis
5,866,340 A   2/1999 Vogelstein et al.
6,307,036 B1  10/2001 Milner et al.
6,326,464 B1  12/2001 Conseiller et al.
6,388,062 B1  5/2002 Halazonetis et al.
6,420,118 B1  7/2002 Halazonetis et al.
2002/0193561 A1 12/2002 Conseiller et al.
2003/0049699 A1 3/2003 Conseiller et al.

FOREIGN PATENT DOCUMENTS

WO    WO 01/18037 A2    3/2001
WO    WO03105880    * 12/2003

OTHER PUBLICATIONS

Seq search result.*
Reed et al., PNAS vol. 92, p. 9455-9459, 1995.*
P53 sequence search of SEQ ID No. 1.*
Kim, Arianna L. (1999) "Conformational and molecular basis for induction of apoptosis by a p53 C-terminal peptide in human cancer cells." *The Journal of Biological Chemistry.* 274:49 34924-34931.
Zakut-Houri, Rina et al. (1985) "Human p53 cellular tumor antigen: cDNA sequence and expression in COS cells." *The EMBO Journal.* 4:5 1251-1255.
Brandt-Rauf, Paul W. (1992) "Conformational Effects of Selected Cancer-Related Amino Acid Substitutions in the p53 Protein" Journal of Biomolecular Structure and Dynamics, 10(2):253-264.

* cited by examiner

*Primary Examiner*—Larry R. Helms
*Assistant Examiner*—Lei Yao
(74) *Attorney, Agent, or Firm*—John P. White; Cooper & Dunham LLP

(57) ABSTRACT

Disclosed are polypeptides comprising a first segment of continuous amino acids having the sequence AQAGKEPGGSRAHSSHLKSKKGQSTSRH-KKLMFKTEGPDSD (SEQ ID NO. 1) covalently linked to a second segment of continuous amino acids having the sequence DSDPGETKFMLKKHRSTSQGKKSKLH-SSHARSGGPEKGAQA (SEQ ID NO. 2), or at least two of each covalently linked to each ether. The polypeptides are shown to induce apoptosis of cancer cells that contain mutant p53 or over-expressed wild-type p53.

16 Claims, 10 Drawing Sheets

Figure 1:
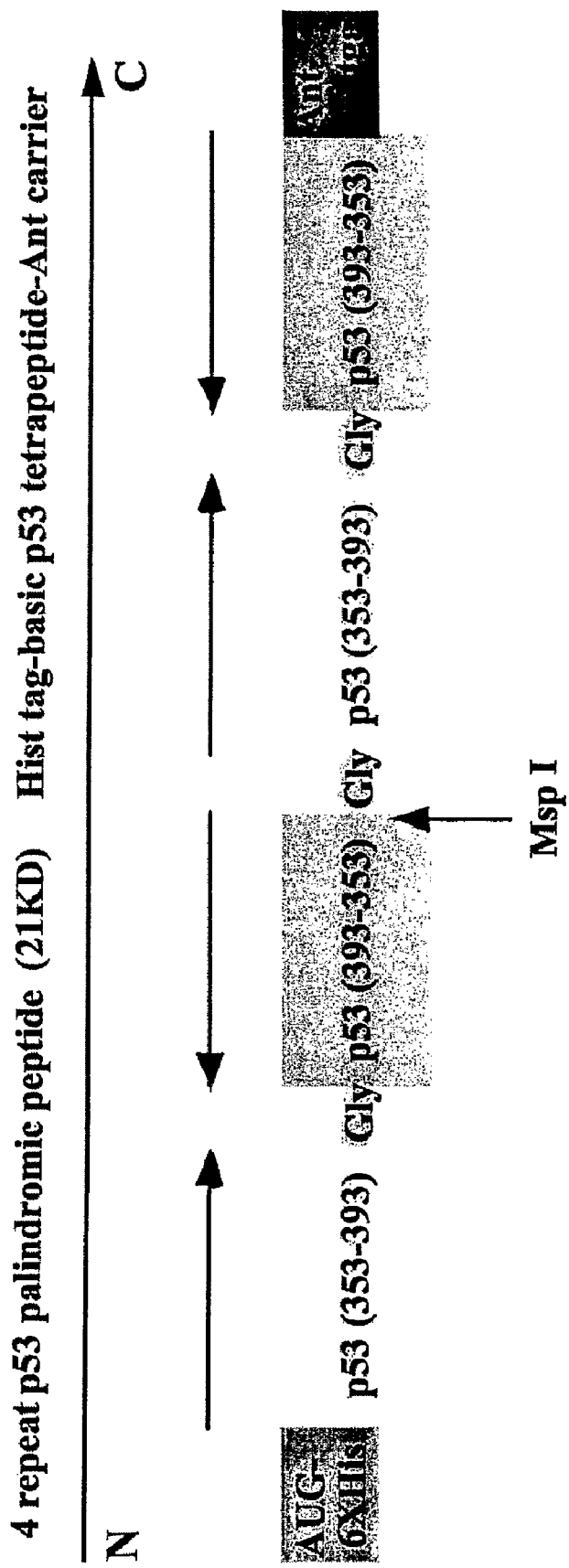

C-TERMINAL P53 PALINDROMIC PEPTIDE THAT INDUCES APOPTOSIS OF CELLS WITH ABERRANT P53 AND USES THEREOF

This application is a §371 national stage of PCT International Application No. PCT/US2005/002543, filed Jan. 27, 2005, and claims the benefit of U.S. provisional application No. 60/540,864, filed Jan. 30, 2004, the contents of all of which are hereby incorporated by reference into this application.

This application claims priority of U.S. Provisional Application No. 60/540,864, filed Jan. 30, 2004, the contents of which are hereby incorporated by reference.

This invention has been made with government support under National Science Foundation grants R01 OH07590, and R01 CA82528. Accordingly, the U.S. Government may have certain rights in the invention.

Throughout this application, various publications are referenced within parentheses. Disclosures of these publications in their entireties are hereby incorporated by reference into this application to more fully describe the state of the art to which this invention pertains.

BACKGROUND OF THE INVENTION

More than 50% of human malignancies, including breast cancers, are associated with missense mutations or deletions of p53, and most of the missense mutations map to the DNA-binding domain of the protein. The nucleotide sequence of the human p53 gene and the amino acid sequence of the encoded p53 protein have been reported (Zakut-Houri et al. (1985), EMBO J., 4: 1251-1255; GenBank Code Hsp53). The p53 protein consists of 393 amino acids and its functional domains have been characterized (e.g., U.S. Pat. No. 6,326,464).

p53 is a sequence-specific transcriptional factor that transactivates a number of genes whose products are involved in cell growth regulation. These include WAF1/p21/Cip1, which arrests the cell cycle, GADD45 for DNA repair, and Bax and Fas/APO-1 to modulate apoptosis. Apoptosis is a complex process regulated by several pathways, some of which involve members of the Bcl-2 family and the Fas pathway. Wild-type p53 forms a tetramer to perform its tumor suppressor activity.

The sequence-specific DNA-binding activity of p53 appears to be negatively regulated by its C-terminal 30-amino acid (aa) segment (aa 363-393) and also by N-terminal proline-rich motifs located between aa 80-93. Synthetic peptides corresponding to the C-terminal domain of p53 such as residues aa 363-393 bind directly in vitro to over-expressed wild-type and mutant p53. Binding experiments with p53 proteins that contain selected deletions indicate that binding of the free aa 363-393 peptide to p53 requires the presence of both C-terminal aa 363-393 and N-terminal aa 80-93 sequences in the p53 protein. This observation suggests either that the free peptide may interact simultaneously with both regions or that the absence of either or both of these segments in p53 results in structural changes in the protein, lowering its affinity for the free peptide.

Deletion of either or both of these regulatory regions, as well as various C-terminal modifications, stimulate specific DNA binding of p53 in vitro. Previous studies demonstrate that the addition of a chemically modified C-terminal p53 peptide restored in vitro sequence-specific DNA binding function to mutant p53-273 (Arg to His). Furthermore, intranuclear microinjection of this peptide into SW480 colon carcinoma cells carrying an endogenous p53-273 His mutation restored transcriptional activation of a p53-responsive reporter construct.

It was previously demonstrated that a synthetic peptide derived from the C-terminal regulatory region of the p53 tumor suppressor protein (amino acids 361-382) could induce p53-dependent, apoptotic cell death in the presence of mutant p53 with minimal effect on cells with normal levels of wild-type 53 (A. L. Kim et al., *Conformational and molecular basis for induction of apoptosis by a C-terminal peptide in human cancer cells*, J. Biol. Chem. (1999) 274:34924-34931). Since p53 mutations occur in over 50% of common human cancers, a therapy directed at specifically killing p53-mutant cells would have wide application.

SUMMARY OF THE INVENTION

An embodiment of the inventions is a polypeptide comprising a first segment of continuous amino acids having the sequence AQAGKEPGGSRAHSSHLKSKKGQSTSRH-KKLMFKTEGPDSD (SEQ ID NO. 1) covalently linked to a second segment of continuous amino acids having the sequence DSDPGETKFMLKKHRSTSQGKKSKLH-SSHARSGGPEKGAQA (SEQ ID NO. 2).

Another embodiment of the invention is a polypeptide comprising at least two covalently linked segments of continuous amino acids, each segment comprising consecutive amino acids having the sequence AQAGKEPGGSRAH-SSHLKSKKGQSTSRHKKLMFKTEGPDSD (SEQ ID NO. 1), or consecutive amino acids having the sequence DSD-PGETKFMLKKHRSTSQGKKSKLH-SSHARSGGPEKGAQA (SEQ ID NO. 2).

A further embodiment of the inventions is a nucleic acid comprising nucleotides encoding any of the disclosed polypeptides, and a plasmid which expresses any of the disclosed polypeptides.

Yet another embodiment of the invention is a method of killing cancer cells that contain mutant p53 or over-expressed wild-type p53 by contacting the cancer cells with the disclosed polypeptides, and a method of treating a subject suffering from cancer by administering to the subject the disclosed polypeptides.

DETAILED DESCRIPTION OF THE FIGURES

FIG. 1

Construction of C-Terminal p53 palindromic tetrapeptide.

FIG. 2

Purification of bacterial lysate produced His-tagged-p53 4-repeat-Ant carrier peptide. Bacterial lysates were first applied to the Nickel-nitrilotriactic column. The histidine amino acids of the 6-His tag bind to the nickel ions immobilized by the nitrilotriactic groups on the agarose matrix. The column is then washed with low concentrations of imidazole (25 mM) to remove nonspecific, low affinity endogenous bacterial proteins (not shown). Increasing the concentration of imidazole from 50 mM (E1), to 100 mM (E2), to 150 mM (E3), and finally to 250 mM (E4), displaces the histidine from the nickel ions so that the tagged protein is removed. Then acrylamide displaces the histidine from the nickel ions so that the tagged protein is removed. This acrylamide (12%)/SDS PAGE gel was stained with 0.25% Ponceau Red solution. STD-protein standards.

FIG. 3

Effects of the C-Terminal p53 Palindromic Tetrapeptide on Cells in Culture. MDA-MB-468 human breast cancer cells were grown in culture and exposed for 6 hours with no peptide (control) or with 30 μM of either the single p53 C-terminal peptide fused to the Ant carrier (p53-Ant) or with the His tagged p53 palindromic tetrapeptide fused to the Ant carrier (4 Repeat). The DNA within the cells was then stained with propidium iodide and cell particles were assayed by flow cytometry. The percent within each graph represents the percent cell particles with less than a diploid amount of DNA, indicative of apoptotic cells (sub G1 population).

FIG. 4

Effects of endogenous, regulated expression of the 4 repeat peptide on cell viability. MDA-MB-468 cells engineered to express the palindromic p53 4 repeat peptide under the control of a tetracycline responsive promoter were cultured without or with the addition of 2 μg/ml doxycycline, an analog of tetracycline, for 24, 48 or 72 hours. Cells were collected, fixed in ice cold 70% ethanol and the DNA was stained with propidium iodide. Cell cycle profiles were obtained by flow cytometry and the percent of sub-G1 cell particles, indicative of apoptosis, was quantified.

FIG. 5

Changes in the protein expression levels for the pro-apoptotic protein Bax, an active p53 responsive gene, induced by exposure to the tetracycline analog doxycycline (2 μg/ml) for 12, 36 and 48 hours. Engineered MDA-MB-468 cells were collected after the indicated exposure times and the total protein was extracted, an aliquot was run on a 12% acrylamide/SDS PAGE gel, and blotted onto nitrocellulose membranes. Antibodies specific for Bax, the 4-repeat (p53) and PARP were used to determine expression levels and α-tubulin was used as a loading control. A PARP cleavage product, indicative for apoptosis, is observed even 12 hours after 4-repeat induction and expression. Of note, the 4 repeat (C-terminal palindromic tetrapeptide) induced Bax while our previous studies have shown that the monomer, p53 peptide-Ant, did not.

FIG. 6

Changes in the protein expression levels for the p53 responsive genes encoding Fas and caspase 8, 24 hours after the engineered MDA-MB-468 cells were exposed to the indicated concentrations of doxycycline. A PARP cleavage product is also shown. α-tubulin was used as a loading control.

FIG. 7

TUNEL assay on engineered MDA-MB-468 human breast cancer cells after 24 hours of exposure to 2 μg/ml Doxycycline. Regulated expression of the p53 4 repeat peptide results in the endonuclease cleavage of chromatin DNA, as seen as a shift from no doxycycline (control) to 24 hours after Doxycycline (Dox 2 μg/ml). If the caspase 8 specific inhibitor (IETD-FMK) at 2 μM is added 6 hours after doxycycline is added, then no shift occurs 18 hours later (24 hr total doxycycline treatment).

FIG. 8

Propidium labeled DNA, indicative of apoptosis, induced by the monomer p53 peptide-Ant and the tetrapeptide (4 repeat)±Ant. Constructs of the plasmids were transfected into DU-145 human prostate cancer cells, which carry an endogenous mutant p53, by adenovirus vector using a multiplicity of infection (MOI) of 50. In addition, these plasmids encoded green fluorescent protein (GFP) as a way to check for successful transfection into the DU-145 cells. The only cells which died were those which received the 4 repeat (C-terminal palindromic tetrapeptide) in their construct with or without Ant. Thus, the short monomeric p53 peptide-Ant was proteolyzed too quickly for its activity to manifest while the 4 repeat exhibited stability and thus induced cell death.

FIG. 9

Ad/4-rep-p53p induced cell deaths in rat glioma 9L cells in a time-dependent manner by TUNEL assay. Three groups of 9L mutant p53 rat glioma cells with either no infection (control), infection with Ad/pCMV-IRES-GFP adenovirus vector control, or infection with Ad/4-rep-p53-p adenovirus which contains the plasmid encoding the C-terminal p53 tetrapeptide were assayed. At 24, 36, and 48 hours, untreated control cells showed 2%, 3%, and 5% cell death, respectively. Cells infected with the Ad/pCMV-IRES-GFP adenovirus which did not contain the peptide showed 4%, 4%, and 8% cell death, respectively. Finally, cells infected with Ad/4-rep-p53p Adenovirus containing the C-terminal p53 palindromic tetrapeptide showed 28%, 34%, and 43% cell death, respectively.

FIG. 10

Survival analysis of male rats initially injected with 5 μl of $10^5$ 9L cells over 10 days (Tumor implantation) through a catheter stereotactically inserted into the right caudate nucleus. These rats were subsequently infused with 7-8 μl volumes per day over 3 hours a day for a total of 7 days in three groups as follows: 2 rats received phosphate buffered saline (PBS control) solution, 3 rats received Ad/vector control virus (Empty Virus Control), and 10 rats received Ad/4-rep-p53p adenovirus containing the tetrapeptide C-terminal p53 peptide.) The average survival time for the groups were: 20 days for the PBS control group, 27 days for the adenovirus vector control group (23.25 days for the combined control groups) and 37.25 days for the Ad/4-rep-p53p Adenovirus treated group. Thus, the treatment group infected with the adenovirus containing the C-terminal palindromic tetrapeptide experienced an 86% increase in survival compared to the PBS controls and a 60% increase in survival compared to the combined controls. The difference in the average survival between the combined control group and the treatment group was statistically significant ($p<0.01$)

DETAILED DESCRIPTION OF THE INVENTION

An embodiment of the inventions is a polypeptide comprising a first segment of continuous amino acids having the sequence AQAGKEPGGSRAHSSHLKSKKGQSTSRH-KKLMFKTEGPDSD (SEQ ID NO. 1) covalently linked to a second segment of continuous amino acids having the sequence DSDPGETKFMLKKHRSTSQGKKSKLH-SSHARSGGPEKGAQA (SEQ ID NO. 2).

The polypeptide may further comprise a glycine between the first segment and the second segment In an embodiment, the polypeptide may comprise amino acids having the palindromic sequence AQAGKEPGGSRAHSSHLKSKKGQSTSRH-KKLMFKTEGPDSD[glycine]DSDPG ETKFM-LKKHRSTSQGKKSKLHSSHARSGGPEKGAQA (SEQ ID NO. 3), wherein the glycine may be present or absent.

In another embodiment, the polypeptide may comprise amino acids having the palindromic sequence DSDPGETK-FMLKKHRSTSQGKKSKLHSSHARSGGPEKGAQA[glycine]AQAGK EPGGSRAHSSHLKSKKGQSTSRHKKLM-FKTEGPDSD (SEQ ID NO. 4), wherein the glycine may be present or absent.

In yet another embodiment, the polypeptide may comprise amino acids having the palindromic sequence AQAGKEPGGSRAHSSHLKSKKGQSTSRH-KKLMFKTEGPDSD[glycine]DSDPG ETKFM-LKKHRSTSQGKKSKLHSSHARSGGPEKGAQA[glycine]AQAGKEPGGS RAHSSHLKSKKGQSTSRHKKLMFKTEGPDSD[glycine]DSDPGETKFMLKKHR STSQGKKSKLHSSHARSGGPEKGAQA (SEQ ID NO. 5), wherein the glycine may be present or absent.

In a further embodiment, the polypeptide may comprise amino acids having the palindromic sequence DSDPGETKFMLKKHRSTSQGKKSKLHSSHARSGGPEKGAQA[glycine]AQAGK EPGGSRAHSSHLKSKKGQSTSRHKKLMFKTEGPDSD[glycine]DSDPGETKFM LKKHRSTSQGKKSKLHSSHARSGGPEKGAQA[glycine]AQAGKEPGGSRAHSS HLKSKKGQSTSRHKKLMFKTEGPDSD (SEQ ID NO. 6), wherein the glycine may be present or absent.

In yet a further embodiment, the polypeptide may comprise amino acids having the palindromic sequence AQAGKEPGGSRAHSSHLKSKKGQSTSRHKKLMFKTEGPDSDDSDPGETKFMLKKH RSTSQGKKSKLHSSHARSGGPEKGAQAAQAGKEPGGSRAHSSHLKSKKGQSTSRH KKLMFKTEGPDSDDSDPGETKFMLKKHRSTSQGKKSKLHSSHARSGGPEKGAQA (SEQ ID NO. 7).

In another embodiment of the invention, the polypeptide comprises at least two covalently linked segments of continuous amino acids, each segment comprising consecutive amino acids having the sequence AQAGKEPGGSRAHSSHLKSKKGQSTSRHKKLMFKTEGPDSD (SEQ ID NO. 1), or consecutive amino acids having the sequence DSDPGETKFMLKKHRSTSQGKKSKLHSSHARSGGPEKGAQA (SEQ ID NO. 2). The polypeptide of this embodiment can contain three or four of the segments covalently linked.

Any of the described polypeptides may further comprise a six repeat histidine tag attached to the N-terminus of the polypeptide.

Any of the described polypeptides may further comprise a membrane carrier peptide attached to the C-terminus of the polypeptide. The membrane carrier peptide may comprise amino acids having the sequence KKWKMRRNQFWVKVQRG (SEQ ID NO. 8).

Any of the described polypeptides may further comprise, together, a six repeat histidine tag attached to the N-terminus of the polypeptide, and a membrane carrier peptide attached to the C-terminus of the polypeptide.

A further embodiment of the inventions is a nucleic acid comprising nucleotides encoding any of the disclosed polypeptides, and a plasmid which expresses any of the disclosed polypeptides.

Another embodiment of the invention is a viral construct containing a plasmid which expresses any of the disclosed polypeptides.

Yet another embodiment of the invention is a method of killing cancer cells that contain mutant p53 or over-expressed wild-type p53 by contacting the cancer cells with the disclosed polypeptides, and a method of treating a subject suffering from cancer by administering to the subject the disclosed polypeptides.

A further embodiment of the invention is a method of killing cancer cells that contain mutant p53 or over-expressed wild-type p53 by infecting the cancer cells with a viral construct containing a plasmid which expresses any of the disclosed polypeptides, and a method of treating a subject suffering from cancer by infecting the subject with a viral construct containing a plasmid which expresses any of the disclosed polypeptides.

Another embodiment is the use of a viral construct containing a plasmid which expresses any of the disclosed polypeptides in the manufacture of a medicament for treating cancer.

Yet another embodiment is a pharmaceutical composition comprising a viral construct containing a plasmid which expresses any of the disclosed polypeptides and a pharmaceutically acceptable carrier for treating cancer.

A further embodiment is the use of any of the disclosed polypeptides in the manufacture of a medicament for treating cancer.

Another embodiment is a pharmaceutical composition comprising any of the disclosed polypeptides and a pharmaceutically acceptable carrier for treating cancer.

Yet another embodiment is a method of inducing apoptosis of a cell that contains mutant p53 or over-expressed wild-type p53 comprising contacting the cell with any of the disclosed polypeptides.

A further embodiment is a method of inducing apoptosis of a cell that contains mutant p53 or over-expressed wild-type p53 comprising infecting the cell with a viral construct containing a plasmid which expresses any of the disclosed polypeptides.

Another embodiment is a pharmaceutical composition comprising a viral construct containing a plasmid which expresses any of the disclosed polypeptides and a pharmaceutically acceptable carrier for inducing apoptosis of a cell that contains mutant p53 or over-expressed wild-type p53.

A further embodiment is a pharmaceutical composition comprising any of the disclosed polypeptides and a pharmaceutically acceptable carrier for inducing apoptosis of a cell that contains mutant p53 or over-expressed wild-type p53.

The ability of the described polypeptides and compositions of this invention to activate the DNA binding activity of p53 and thus activate the cellular functions of p53, enables their use as pharmaceutical compositions in a variety of therapeutic regimens. The present invention therefore includes novel therapeutic pharmaceutical compositions and methods for treating a human or animal with such compositions. As used herein, the term "pharmaceutical" includes veterinary applications of the invention.

To prepare the pharmaceutical compositions of the present invention, at least one polypeptide, or alternatively, a mixture of polypeptides of this invention is combined as the active ingredient in admixture with a pharmaceutical carrier selected and prepared according to conventional pharmaceutical compounding techniques. This carrier may take a wide variety of forms depending on the form of preparation desired for administration, e.g., oral, sublingual, rectal, nasal, parenteral intraperitoneal, intravenous, intraarterial.

Pharmaceutically acceptable solid or liquid carriers or components which may be added to enhance or stabilize the composition, or to facilitate preparation of the composition include, without limitation, syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The carrier may also include a sustained release material such as glyceryl monostearate or glyceryl distearate, alone or with a wax. The amount of solid carrier varies but, preferably will be between about 20 mg to about 1 g per dosage unit.

Pharmaceutical compositions of the peptides of this invention, or derivatives thereof, may therefore be formulated as solutions of lyophilized powders for parenteral administration. Another method of administration is that of intravenous or intraarterial administration.

Pharmaceutical compositions of this invention may also include topical formulations incorporated in a suitable base or vehicle, for application at the site of the area for the exertion of local action. Accordingly, such topical compositions include those forms in which the formulation is applied externally by direct contact with the skin surface to be treated. Conventional forms for this purpose include but are not limited to, creams, ointments, lotions, gels, pastes, powders and formulations having oleaginous absorption, water-soluble, and emulsion-type bases.

Additionally, the compounds of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

Dosage units of such pharmaceutical compositions containing the polypeptides of this invention preferably contain about 1 mg-5 g of the peptide or salt thereof.

As used herein, the terms "suitable amounts" or "therapeutically effective amount" means an amount which is effective to treat the conditions referred to below. A polypeptide of the present invention is generally effective when parenterally administered in amounts from 1 mg per kg of body weight to 100 mg/kg.

The pharmaceutical compositions described above and identified with the ability to activate the DNA binding activity of p53 are useful in therapeutic regimens which exploit the cellular functions of p53.

Compositions of this invention may be administered parenterally (for example, intravenously) as an adjunct to patients receiving traditional cancer therapy, which employs the use of DNA damaging agents (eg. radiation therapy and chemotherapy). The compositions of this invention may also be employed as the sole treatment for patients with cancer to enhance the tumor suppressor function of p53, whether wild-type or mutant, present in tumor cells. The administration of the composition to a cancer patient thus permits the arrest of the growth or proliferation of tumor cells or apoptosis (cell death) of tumor cells. A suitable amount of the composition of this invention is administered systemically, or locally to the site of the tumor.

Definitions

A palindrome, or a palindromic sequence, is used herein to mean a polypeptide comprising amino acids having a sequence which is the same when read from the N-terminal to the C-terminal, as when read from the C-terminal to the N-terminal, e.g. "ABCBA" or "ABCCBA".

A "construct" is used to mean recombinant nucleic acid which may be a recombinant DNA or RNA molecule, that has been generated for the purpose of the expression of a specific nucleotide sequence(s), or is to be used in the construction of other recombinant nucleic acids. In general, "construct" is used herein to refer to an isolated, recombinant DNA or RNA molecule.

Viral vector is used herein to mean a vector that comprises all or parts of a viral genome which is capable of being introduced into cells and expressed. Such viral vectors may include native, mutant or recombinant viruses. Such viruses may have an RNA or DNA genome. Examples of suitable viral vectors include retroviral vectors (including lentiviral vectors) (WO 94/06910), adenoviral vectors (WO 94/24297), adeno-associated viral vectors and hybrid vectors.

A retroviral vector is a viral vector where the virus is from the family retroviridae.

Transduction is used to refer to the introduction of genetic material into a cell by using a viral vector.

As used herein a transduced cell results from a transduction process and contains genetic material it did not contain before the transduction process, whether stably integrated into the genome or as an episome.

Transfection refers to the introduction of genetic material into a cell without using a viral vector. Examples of transfection include insertion of "naked" DNA or DNA in liposomes, that is without a viral coat or envelope.

The phrase "pharmaceutically acceptable carrier" is used to mean any of the standard pharmaceutically acceptable carriers. Examples include, but are not limited to, phosphate buffered saline, physiological saline, and water.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intracerebral, intraspinal and intrasternal injection and infusion.

The preparations of the present invention may be given parenterally, orally topically, or rectally. They are of course given by forms suitable for each administration route. For example, they are administered by injection, orally inhalation, ointment, suppository, etc. administration by injection, infusion or inhalation; topical by lotion or ointment; and rectal by suppositories.

Details of general formulation procedures and information on additional excipients may be found in Remington: The Science and Practice of Pharmacy, 20th Edition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

EXPERIMENTAL DETAILS

Production and Isolation of C-Terminal p53 Palindromic Tetramer

A series of primers were designed for PCR to gradually extend the C-terminal peptide codon sequence (amino acids 353-393) so that a second C-terminal peptide codon sequence would be conjugated in reverse to the original sequence; this palindromic sequence was engineered so that an additional codon for the amino acid glycine (CGG) occurred between the two sequences to insure maximum structural flexibility at the junction of the palindromes (i.e., amino acids 353-393-Gly-393-353). An additional codon for the amino acid glycine (CGG) was then inserted downstream of the 5'-terminal 353 alanine codon (GGC), which thereby generated a unique restriction enzyme site for MspI (GGCCGG (SEQ ID NO. 9)). This restriction enzyme site made possible the fusion of two of these dimer codon sequences together to form the codon sequence for a palindromic tetramer (FIG. 1). An additional PCR with unique primers resulted in the insertion of a start methionine codon at the 5' end and a termination codon at the 3' end of the palindromic tetramer codon sequence. Furthermore, additional restriction enzyme sites were generated at both termini of the tetramer construct to facilitate proper expression orientation into any cloning or expression vector. The proper sequence of the final expression construct was confirmed by DNA sequence analysis.

For cloning, in order to generate sufficient peptide we selected a bacterial protein expression system (QIAexpressionist, Qiagen, Valencia, Calif.). All procedures were performed with materials supplied by the manufacturer according to their instructions. At the N-terminus of the tetramer construct a six repeat histidine tag was inserted as part of the pQE plasmid. In addition, at the C-terminus the 17 amino acid coding sequence for the membrane carrier peptide derived from Antennaepedia was inserted to allow for free passage of the expressed peptide through cell membranes. Appropriate restriction enzyme sites (EcoRI at the 5' end and HindIII at the 3' end) were engineered to bracket the start codon-His tag-C-terminal p53 palindromic tetramer-Antennapedia carrier-stop codon sequence. Reconstruction of the supplied plasmid, using PCR with specially designed primers, was necessary to ensure that no additional codons were inserted at any junction point. The final sequence was confirmed by DNA sequence analysis (FIG. 1).

Figure 2:
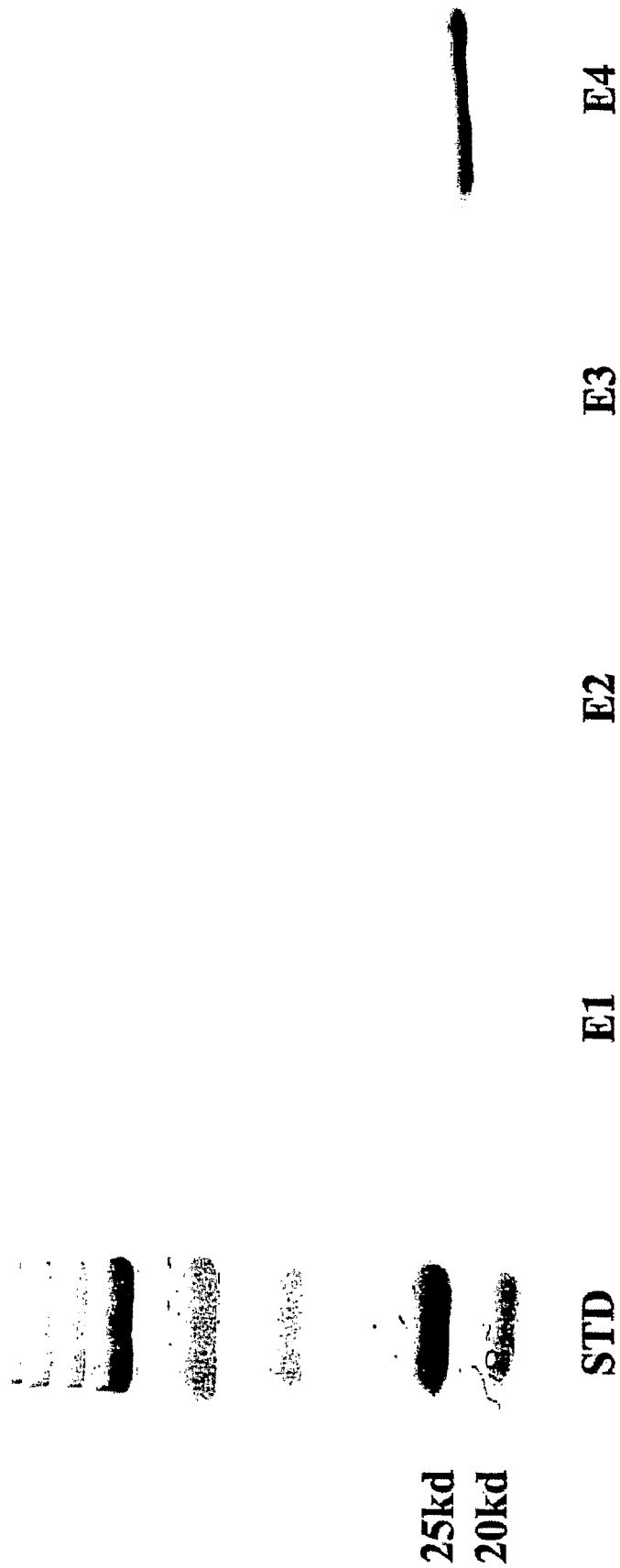

Since this system is designed to produce high levels of the exogenous protein, the production of the product is regulated so that bacteria can replicate and cultures can be established. Once sufficient *E. coli* containing the construct has been cultured, isopropyl-(3-D-thiogalactoside (IPTG) is added to the cultures to stimulate exogenous protein production. IPTG binds to the trans-expressed lac repressor protein excoded by the lac I gene (a bacterial clone is provided as part of the system and is maintained by co-expression of a kanamycin resistance gene). Multiple copies of the lac repressor gene ensure high expression of the lac repressor, which binds to the operator region and lightly regulates expression of the recombinant exogenous peptide (His tag-C-terminal p53 palindromic tetramer-Antennapedia carrier). A Ni-nitrilotriacetic acid based column, provided as part of the kit, is used to purify the peptide through binding, washing and elution with appropriate buffers for the His tag. The final 21 kD peptide, with a PI of about 9.7, was easily purified from the total bacterial lysate by this approach (FIG. 2).

EXAMPLE 1

A. Transfection and Expression of C-Terminal p53 Palindromic Tetramer in Human Cells For stable transfection into human cancer cell lines, the expression construct was incorporated into an inducible expression system in order to demonstrate the cytotoxic effects in a controlled manner. The MDA-MB-468 breast cancer cell line which expresses high levels of mutant p53 (Arg to His substitution at amino acid 273, one of the two most common p53 mutations in human cancers) was chosen as the model system. The tetracycline-inducible RevTet-On System (Clontech Laboratories, Palo Alto, Calif.) was used for these studies. Stably expressed reverse tetracycline-controlled transactivator (rtTA), under the control of a CMV promoter, was first established in the MDA-MB-468 cell line. Initially immunoblots with an antibody against the transactivator were used to identify high expression; subsequently a luciferase reporter system was used to identify highly inducible clones. This assay incorporated a luciferase reporter (Promega, Madison, Wis.) with the inducible pREvTRE vector of the RevTet-On system to measure the ability of tetracycline to induce luciferase activity. By means of these combined systems several MDA-MB-468 clones were identified which could express minimal luciferase activity without tetracycline exposure yet show high levels of luciferase activity after several hours in the presence of tetracycline. Using these clones, the inducible expression of the palindromic tetramer peptide was constructed in these cells. Additionally, the same inducible clones were used to express several control peptides, including the original single p53 C-terminal peptide, the jellyfish green fluorescent protein (GFP) and the palindromic tetramer fused to GFP. Since the anti-p53 antibody PAb-421 epitope is directed against p53 amino acids 371-380, which is contained in the peptide, measurement of expression of small amounts of the peptide in the inducible MDA-MB-468 model system via immunoblotting was possible. After 24 hours of exposure of these cell sub-lines to the tetracycline analogue doxycycline, measurement of expression of the various peptides and/or the intensity and distribution of GFP was similarly possible.

B. Effects of the C-Terminal p53 Palindromic Tetramer on Cells in Culture

Figure 3:
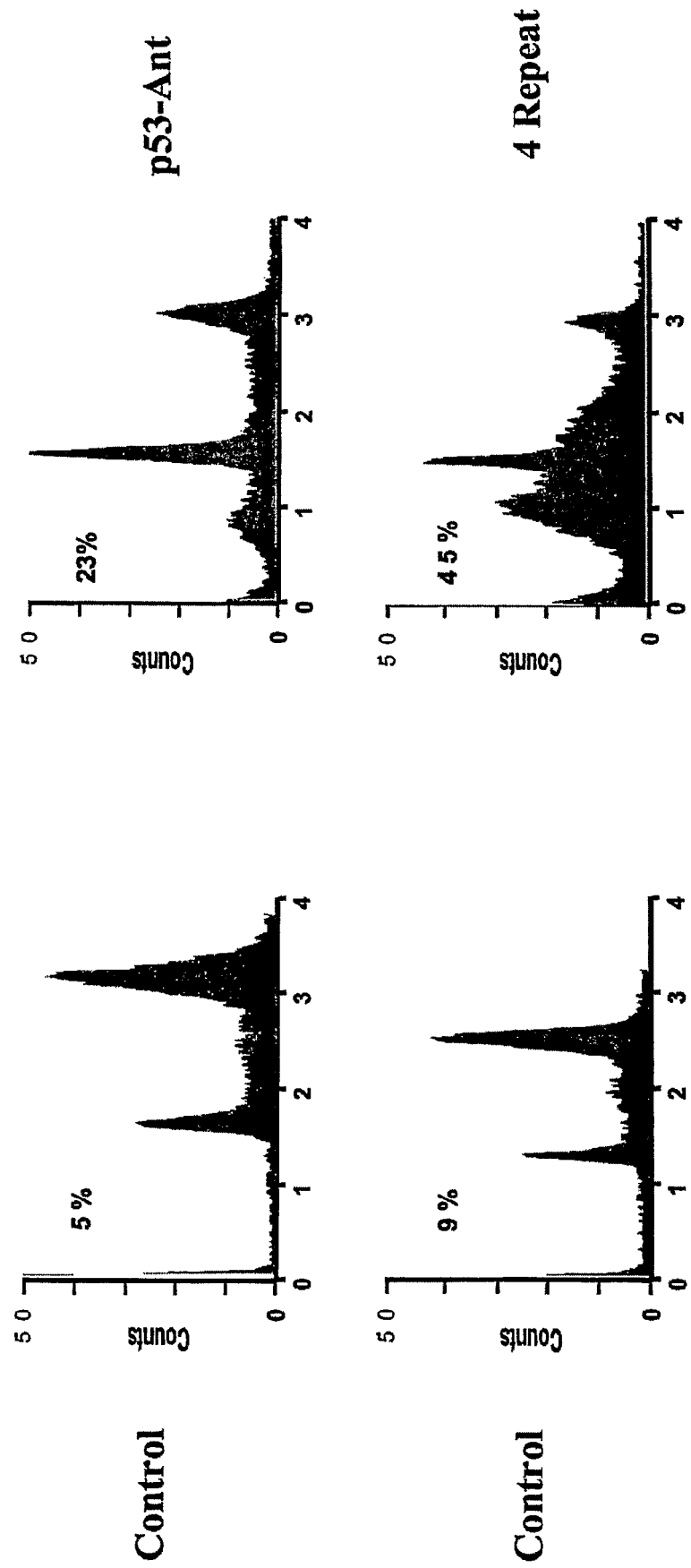

In order to test the effect of the C-terminal p53 palindromic peptide cloned in *E. Coli* on cells in culture, the purified peptide was incubated at 30 μM with the human breast cancer cell line MDA-MB-468, and the effects compared to original monomer or single C-terminal peptide. Prior experiments had shown that exposure at this concentration was less than the $IC_{50}$ for the original peptide. After exposure, the cells were collected, fixed in cold 70% ethanol, and the DNA was stained with propidium iodide. The DNA content was then quantified by flow cytometry in a FACSCalibur Cell Sorter (BD Bioscience, San Diego, Calif.). Cell cycle profiles were obtained, and the percentage of cells containing less than the diploid amount of DNA, indicative of cell undergoing cell death by apoptosis (sub-G1 peak), was quantified (FIG. 3). Palindromic peptide treatment of MDA-468 at 30 uM for 6 hours showed 45% cell death whereas p53 C-terminal peptide (single repeat) showed 23% cell death (PI staining). This comparison shows that the C-terminal p53 palindromic peptide is about twice as effective in inducing apoptosis as the original single peptide sequence on an equimolar basis.

Figure 4:
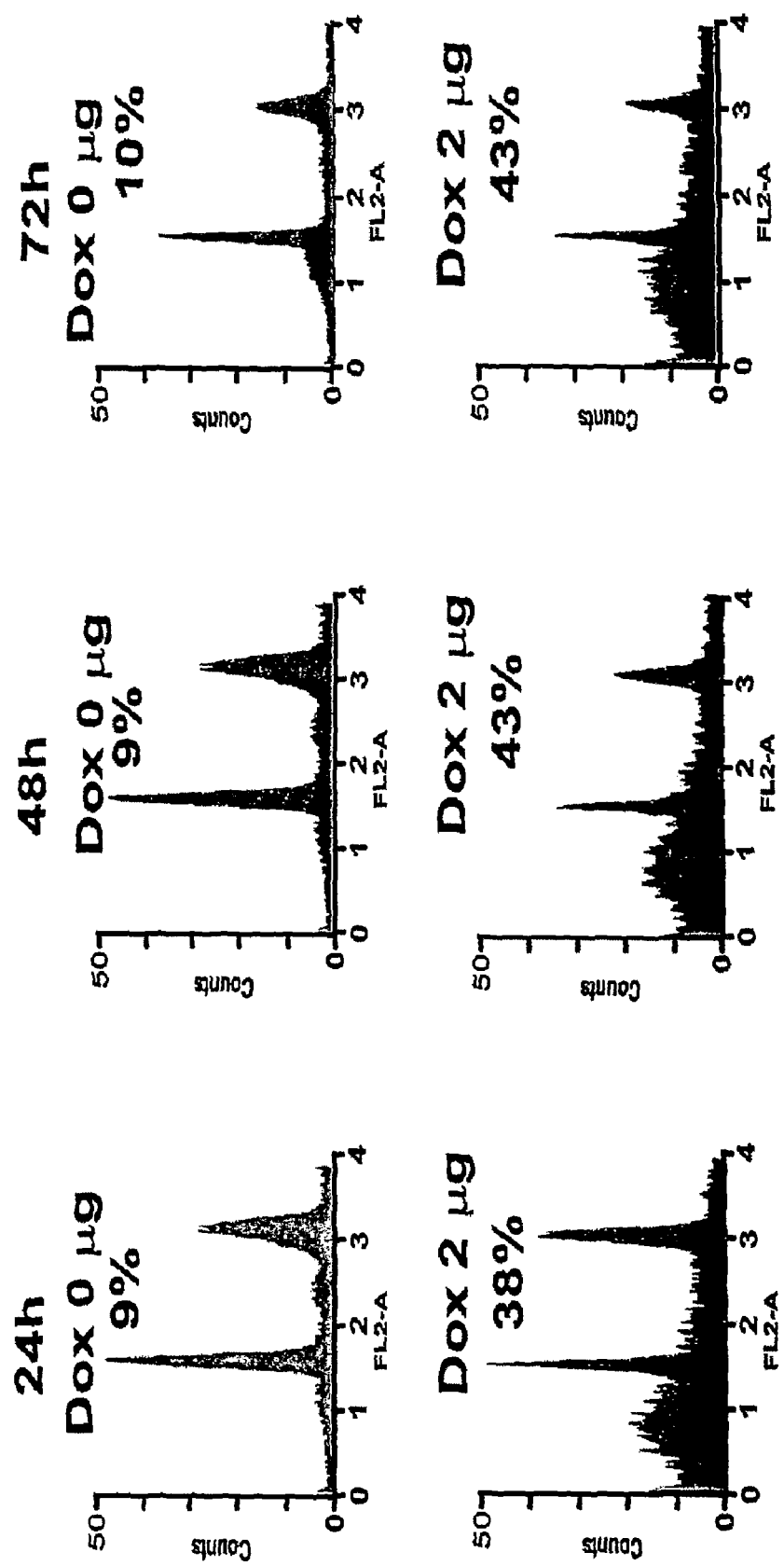
Figure 5:
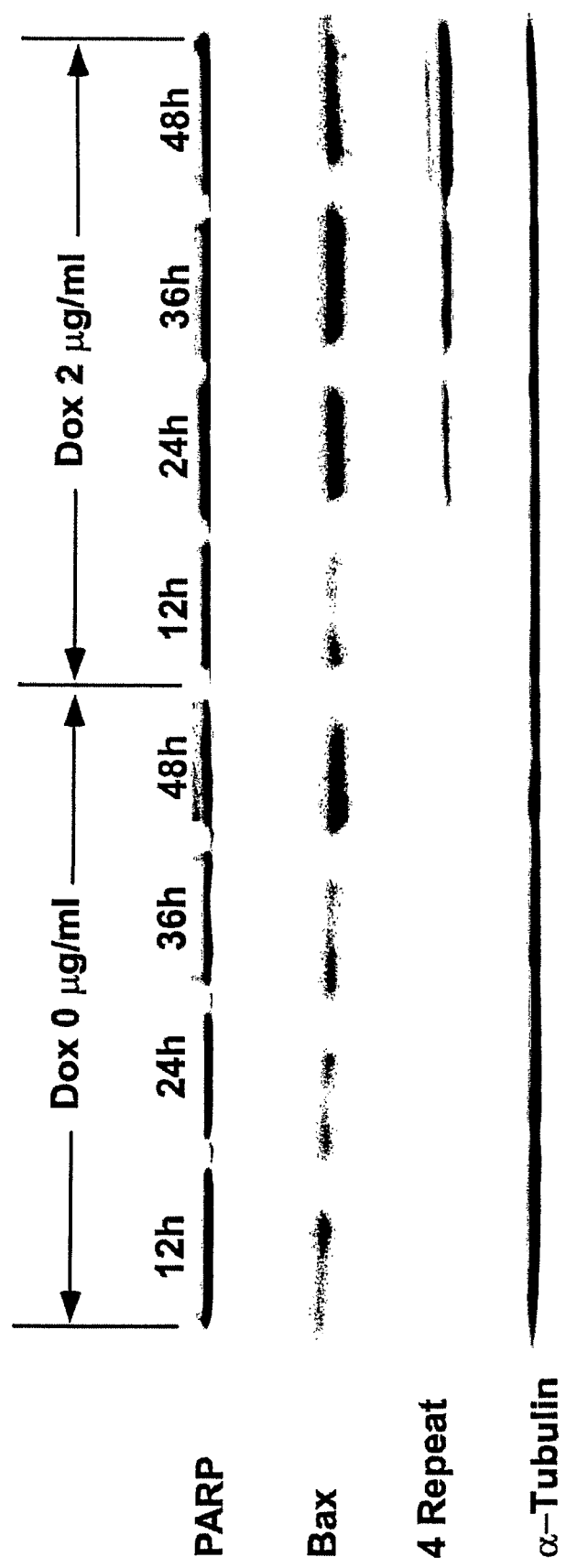
Figure 6:
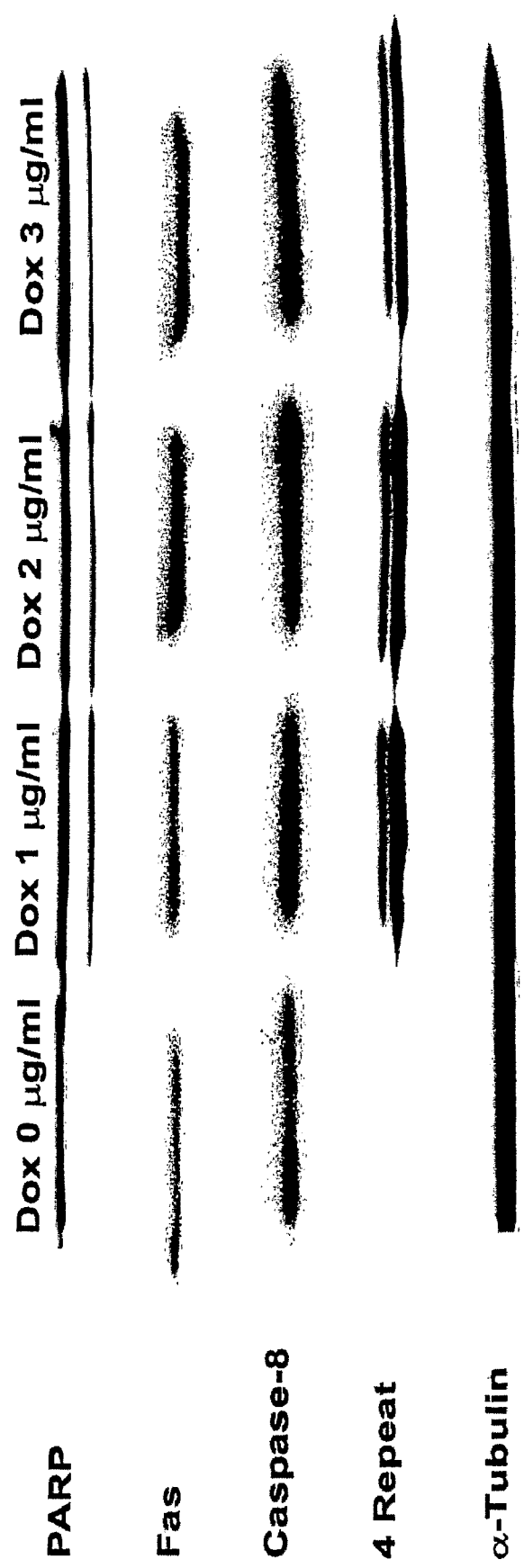

For the tetracycline-inducible peptide systems in MDA-MB-468 cells, cells were exposed to various concentrations of doxycycline for 24-48 hours and cell death measured by trypan blue exclusion (only dying cells are permeable to this dye) and propidium iodide staining (as above, in cells undergoing apoptosis DNA is cleaved so less PI can be bound resulting in accumulation of a sub-G1 peak of cells on flow cytometry). By trypan blue exclusion, control GFP cells showed approximately a 17% decrease in viability, cells expressing the single C-terminal sequence showed approximately a 30% decrease in viability, and cells expressing the p53 palindromic tetramer showed greater than 80% decrease in viability. As measured by propidium iodide staining for the sub-G1 peak of cells on flow cyctometry, the P53 C-terminal 4-repeat cells, which stably express the 4-repeat under doxycycline regulation showed 43% cell death after induction whereas a control cell line, which inducibly expresses GFP showed background levels of 9%. By propidium iodide staining and flow cytometry, control GFP cells showed 12-15% apoptosis, cells expressing the single C-terminal sequence showed approximately 30% apoptosis, and cells expressing the p53 palindromic tetramer showed greater than 40% apoptosis (FIG. 4). In the latter cells, there were also demonstrable changes in the expression of p53 responsive proteins, including an increase in the expression of the pro-apoptotic protein Bax (FIG. 5), Fas and caspase 8, which is the initial caspase activated in the Fas death pathway (FIG. 6). Interestingly, Bax expression from the 4 repeat is unique because the monomer, single p53 peptide, does not induce Bax, only the Fas related mechanism of apoptosis. This suggests that the 4 repeat can restore two targets of functional p53 where the monomer only restores one function. This implies a unique difference between the monomer and the 4 repeat.

Figure 7:
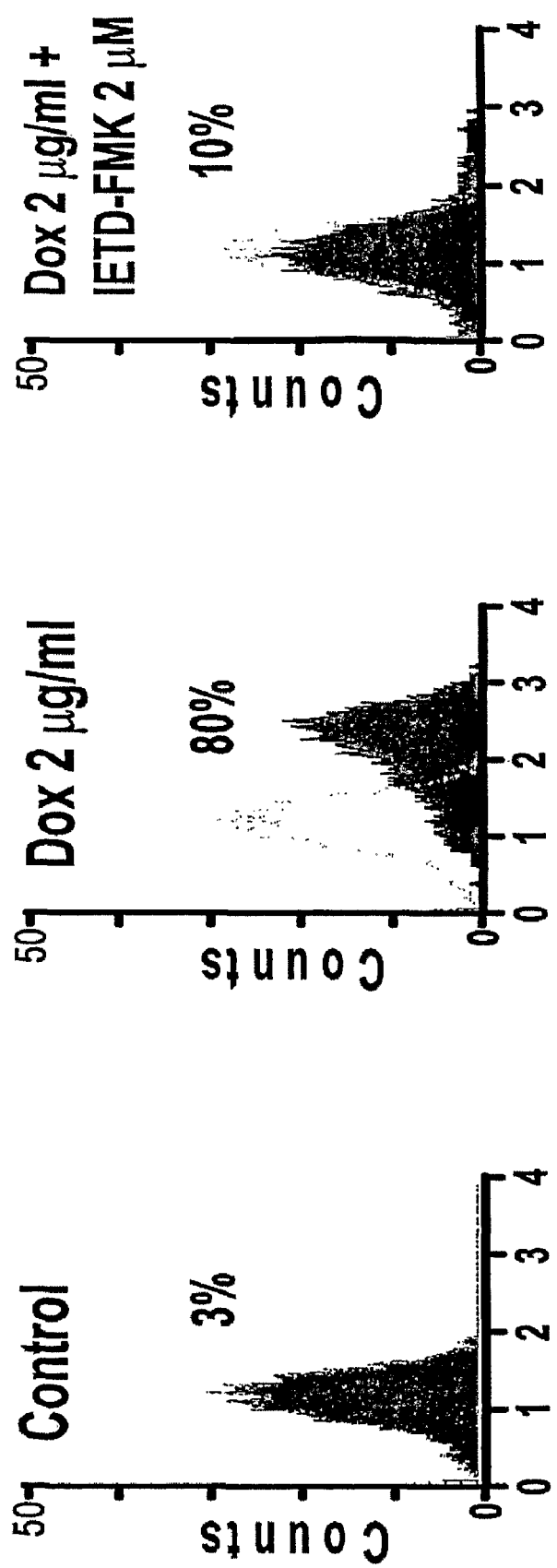

Furthermore, using a specific inhibitor for caspase 8 eliminated the death induced by the C-terminal p53 palindromic tetrapeptide expression. The cleavage of the DNA repair signal protein poly-adenosyl-ribose polymerase (PARP), a key indicator of apoptosis, was also observed with the C-terminal p53 palindromic tetramer expression (FIGS. 5 and 6). Finally, one of the later events to occur as cells are undergoing apoptosis is the endonuclease cleavage of chromatin DNA at the DNA linker site between nucleosomes. These DNA fragments can be end-labeled with fluorescent-dUTP with the use of terminal deoxynucleotidyl transferase. This technique, called TUNEL, is extremely sensitive for the detection of apoptosis. We used a commercial TUNEL assay (Medical & Biological Labs, Nagoya, Japan) with flow cytometry to examine these engineered cells. By this assay, 80% of the cells were killed with induction of the 4 repeat by doxycycline treatment (FIG. 7). Furthermore, by using a specific inhibitor for caspase 8, IETD-FMK (Molecular & Biological Labs, Nagoya, Japan), death induced by the C-terminal p53 palindromic peptide expression (FIG. 7) was eliminated. All of these findings support an apoptotic mechanism of cell death by this peptide.

It was also noted that the tetrapeptide has no to minimal effect on normal cells including the pluripotent stem cells for granulocytes, erythrocytes, monocytes and macrophages. It is taken up by all cells, but only kills cells that contain mutant p53.

C. Effects of Expression of the C-Terminal p53 Palindromic Tetramer in Animals

As a first step in demonstrating the efficacy of the palindromic tetramer to induce apoptosis of cancer cells in vivo, inducible expression is tested in athymic nude mice. The MDA-MB-468 parent line has been shown to be tumorigenic in these mice due to their lack of a competent immune system.

Four groups of ten animals each are used. Groups 1 and 2 are injected with one million MDA-MB-468 cells containing the inducibly expressible palindromic tetramer in 0.5 ml of basement membrane media. Groups 3 and 4 are injected with one million MDA-MB-468 cells containing the inducibly expressible GFP. The tumors are allowed to develop to a measurable state (approximately 2-3 weeks). Then groups 1 and 3 are given 0.5 mg/ml doxycycline in their drinking water, and groups 2 and 4 are given drinking water without doxycycline. Tumor sizes are measured daily. Animals are then euthanized and the tumors removed for analysis. Tumor sections are assayed for levels of apoptosis by DNA cleavage assay (TUNEL) and activation of caspases and cleavage of PARP.

The palindromic tetramer is found to induce apoptosis of cancer cells in animals.

EXAMPLE 2

A. Creation of Adenoviral Constructs Expressing C-Terminal p53 Palindromic Tetramer and Infection of Human cells Similarly, plasmid constructs suitable for expression via an adenovirus vector delivery system have been made for the C-terminal p53 peptide with and without Ant and for the tetrapeptide repeat with and without Ant, all with the GFP label. These plasmids are under the control of a CMV promoter (pCMV) and have an IRES segment separating the GFP from the peptide sequences so that both peptides and GFP are expressed simultaneously but independently (i.e., not covalently linked) so that expression can be confirmed by the GFP but the effect is due only to the peptide. The plasmid constructs tested for apoptotic activity thus include:

pCMV-IRES-GFP (control)
pCMV-p53Cterm-IRES-GFP (single repeat without Ant)
pCMV-p53Ant-IRES-GFP (single repeat with Ant)
pCMV-p53Ant-IRES-p53Ant (double dose of single repeat with Ant)
PCMV-4R-IRES-GFP (4 repeat without Ant)
pCMV-4RAnt-IRES-GFP (4 repeat with Ant).

These plasmids were packaged in an adenovirus vector system (Invitrogen, Carlsbad, Calif.) which was allowed to infect DU145 prostate cancer cells (with p53 mutations at 223 val->phe and 274 pro->leu) in culture at a multiplicity of infection of 50. The cells were assayed for apoptosis by propidium iodide staining after 48 hours.

Figure 8:
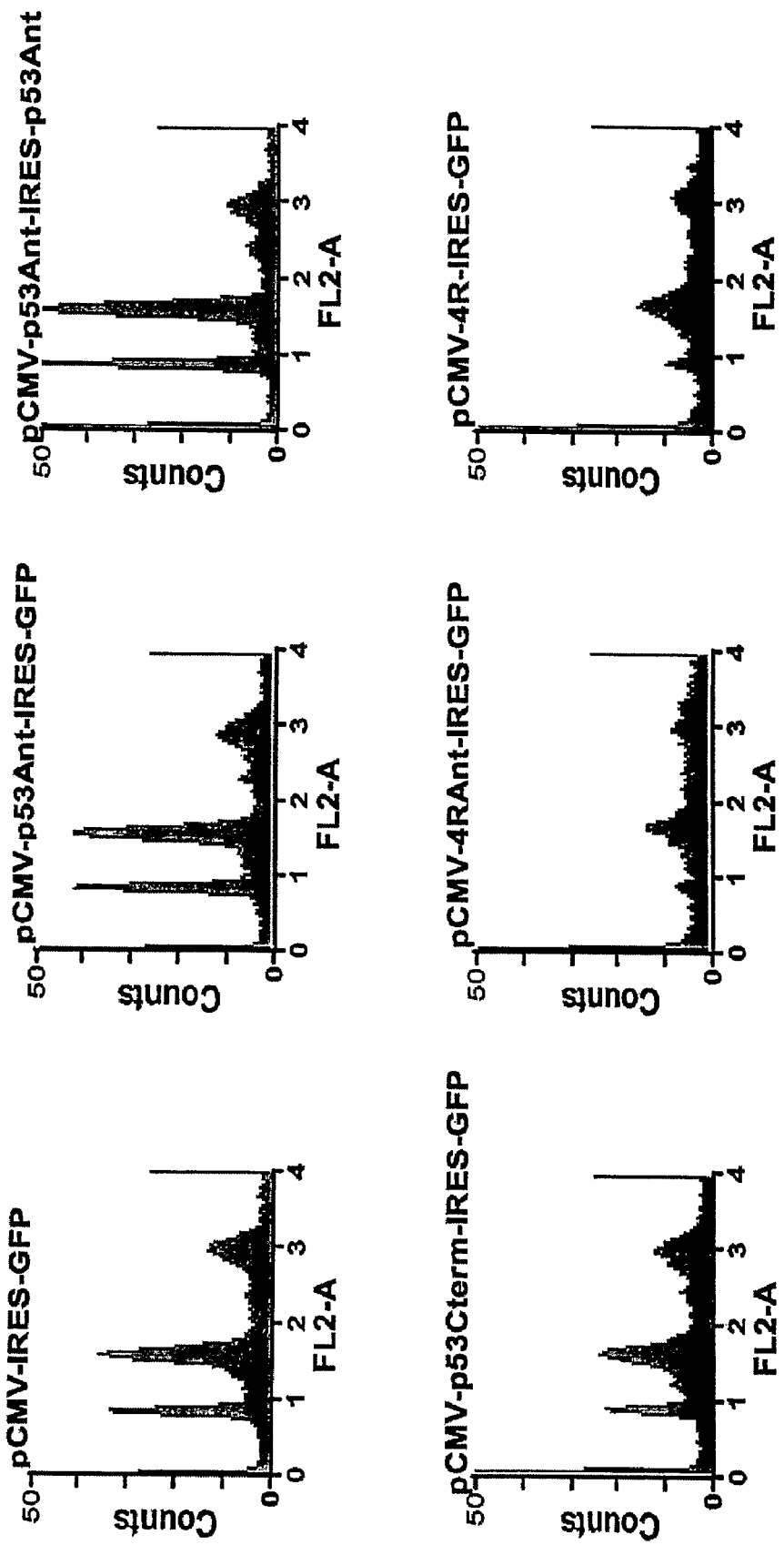

B. Effects of C-Terminal p53 Palindromic Tetramer (Delivered by Adenovirus Infection) on Human Cells in Culture With adenoviral delivery, the control and various single repeat peptide plasmid constructs had minimal effect on DU145 cell viability, despite the fact that they were expressed as evidenced by the GFP label. On the other hand, the palindromic four repeat constructs caused >90% cell death (FIG. 8). This was determined by western blotting to be due at least in part to the short half-life of the single repeat peptides in the cells. This could explain the differences in gene expression seen with the single repeat and four repeat peptides, in particular the fact that the former did not elicit Bax expression but the latter did, and Bax expression is known to require a greater p53 activity. Also, the lack of any significant difference in effect between the single dose and double dose of the single repeat peptide suggests that dose alone is not as important as the fact the peptides in the four repeat are covalently linked and organized in such a fashion that they could mimic a natural p53 tetramer.

EXAMPLE 3

A. Additional Adenoviral Construct Expressing the C-Terminal p53 Palindromic Tetramer and Infection of Rat Glioma Cells Additional plasmid constructs suitable for expression via an adenovirus vector delivery system have been made for the C-terminal p53 palindromic tetrapeptide with an Xho I/EcoRI restriction site. These plasmids were inserted into, an adenovirus construct with the E1/E3 deleted to create an incompetent adenovirus vector Ad/4-rep-p53p and then propagated into the transformed primary embryonal human kidney 293A cells according to the manufacturer's instructions (Invitrogen, Carlsbad, Calif.) The viral particle titer was $3 \times 10^8$ pu/ml as determined by plaque titration assay in the 293A cells. The virus particles were concentrated with Adeno-X Virus Purification Mega Kit, according to the manufacturer's instructions (BD Biosciences Clontech, Palo Alto, Calif.) to a final concentration of $5 \times 10^9$ pu/ml for further studies. The Ad/pCMV-IRES-GFP adenovirus construct without the tetrapeptide sequence was used as the control.

A well established animal model based on intracerebral clysis of syngeneic rat glioma cells was chosen for in vivo testing (Bruce et al., 2000; Kaiser et al., 2000.) The Ad/4-rep-p53p adenovirus vector containing the plasmid encoding the C-terminal p53 palindromic tetrapeptide was allowed to infect 9L mutant p53 rat glioma cells obtained from the ATCC. Adenovirus delivery was first established in cell culture by performing transient infection of the 9L cells with a multiplicity of infection of 50 of Ad/4-rep-p53p Adenovirus or Ad/pCMV-IRES-GFP Adenovirus for 24, 36, and 48 hours. Cells were lysed and analyzed by Western immunoblotting to demonstrate high levels of expression of the peptide. Cells were also fixed in 4% formaldehyde for 1 hour and analyzed by TUNEL assay with the MEBSTAIN Apoptosis Kit Direct (Molecular & Biological Labs, Nagoya, Japan) according to the manufacturer's instructions, to demonstrate cell killing by apoptosis.

Figure 9:
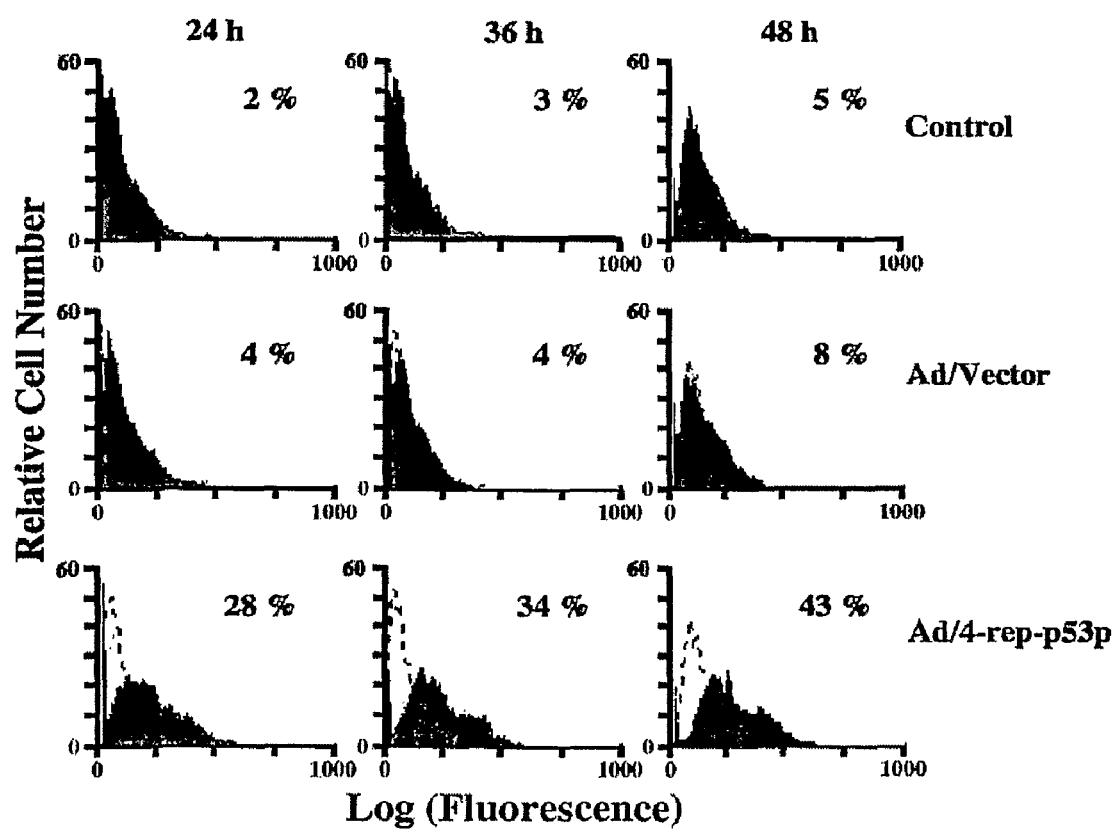

B. Effects of C-Terminal p53 Palindromic Tetramer (delivered by adenovirus infection) on Rat Glioma Cells In the 9L mutant p53 rat glioma cells infected with the Ad/4-rep-p53p Adenovirus containing the C-terminal p53 palindromic tetrapeptide Western Immunoblotting demonstrated effective delivery of the tetrapeptide by the adenovirus and concomitant selective induction of apoptotic cell death. At 24, 36, and 48 hours, untreated control cells showed 2%, 3%, and 5% cell death by the TUNEL assay. Cells infected with the Ad/pCMV-IRES-GFP Adenovirus which did not contain the peptide showed 4%, 4%, and 8% cell death by the TUNEL assay. Finally, cells infected with Ad/4-rep-p53p Adenovirus containing the C-terminal p53 palindromic tetrapeptide showed 28%, 34%, and 43% cell death. (FIG. 9.) These findings support an apoptotic mechanism of cell death by this tetrapeptide.

EXAMPLE 4

A. Infection of Male Fischer Rats with Rat Glioma Cells Containing the Adenoviral Construct Expressing the C-Terminal p53 Palindromic Tetramer For animal studies, 15 male fischer rats (age 12-14 weeks, 250 g) were anesthetized, and a 20 gauge plastic guide cannula was cemented into their skulls. After allowing the rats to recover for 48 hours, a catheter was stereotactically inserted into the right caudate nucleus, and $10^5$ 9L cells in a volume of 5 µl were injected over 10 days. The catheter was withdrawn, the guide cannula was sealed with a dummy stylet, and the tumor cells allowed to grow for 10 days. Then, rats were infused with 7-8 µl volumes per day over 3 hours a day for a total of 7 days in three groups as follows: 2 rats received phosphate buffered saline (PBS) solution, 3 rats received Ad/vector control virus (Ad/pCMV-IRES-GFP), and 10 rats received Ad/4-rep-p53p adenovirus containing the tetrapeptide. The rats were monitored for an additional 44 days to determine differences in survival among groups.

Figure 10:
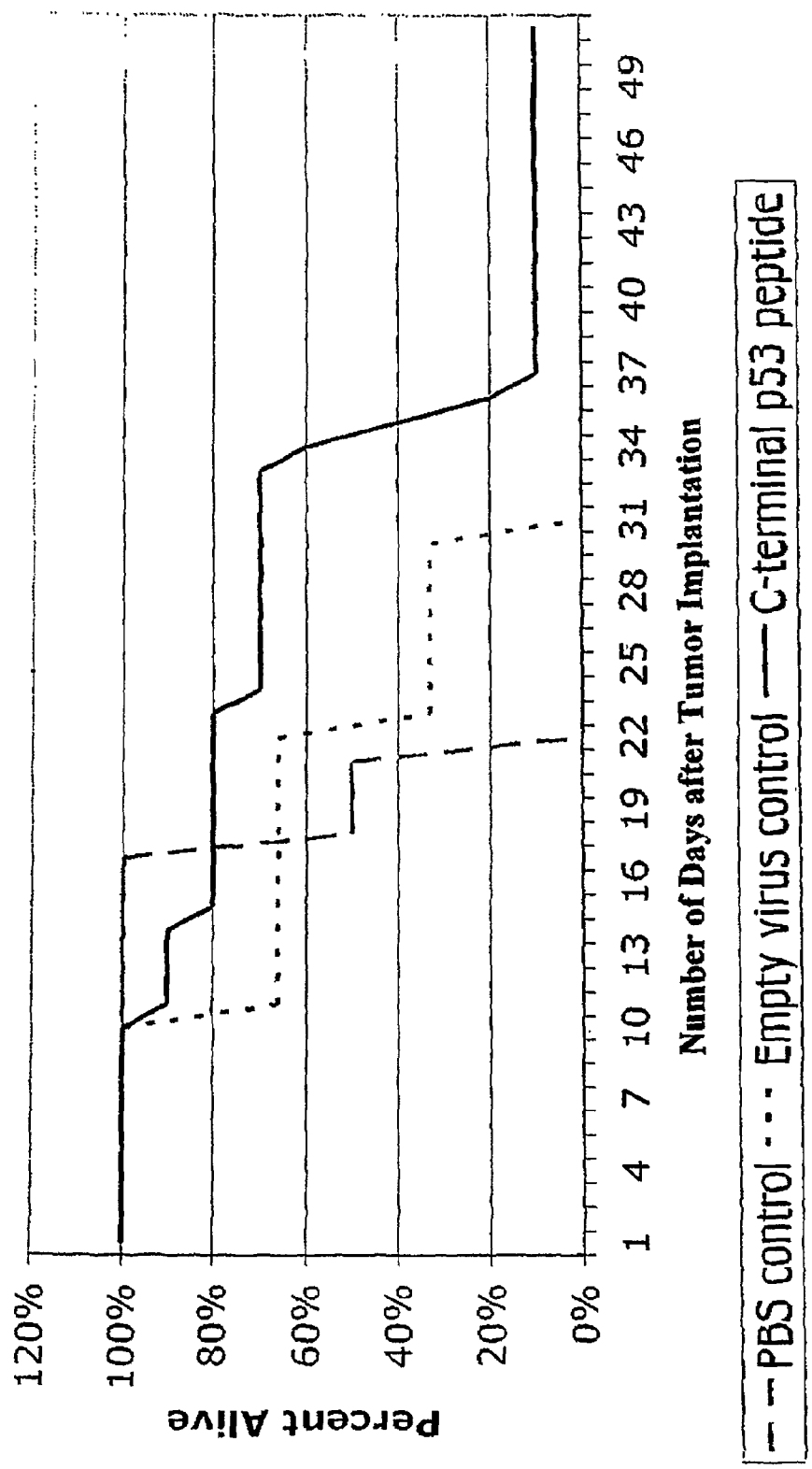

B. Effects of C-Terminal p53 Palindromic Tetramer Delivered by Adenovirus Infected Rat Glioma Cells on Rats In the rats infected with 9L mutant p53 rat glioma cells containing adenovirus constructs, 2 rats in the Ad/4-rep-p53p Adenovirus treatment group and 1 rat in the Ad/pCMV-IRES-GFP Adenovirus vector control group died from the procedures. The remaining rats in each group were followed until death. The average survival time for the groups were: 20 days for the PBS control group, 27 days for the adenovirus vector control group (23.25 days for the combined control groups) and 37.25 days for the Ad/4-rep-p53p Adenovirus treated group. (See FIG. 10.) Thus, the treatment group infected with the adenovirus containing the C-terminal palindromic tetrapeptide experienced an 86% increase in survival compared to the PBS controls and a 60% increase in survival compared to the combined controls. The difference in the average survival between the combined control group and the treatment group was statistically significant ($p < 0.01$)

The palindromic tetramer is found to induce apoptosis of cancer cells in animals.

What is claimed is:

1. A polypeptide comprising consecutive amino acids AQAGKEPGGSRAHSSHLKSKKGQSTSRH-KKLMFKTEGPDSD(glycine)DSDPG ETKFM-LKKHRSTSQGKKSKLHSSHARSGGPEKGAQA (SEQ ID NO:3), wherein the glycine may be present or absent.

2. The polypeptide of claim 1, further comprising a six repeat histidine tag attached to the N-terminus of the polypeptide.

3. The polypeptide of claim 1, further comprising a membrane carrier peptide attached to the C-terminus of the polypeptide.

4. The polypeptide of claim 3, wherein the membrane carrier peptide comprises amino acids KKWKMRRNQF-WVKVQRG (SEQ ID NO:8).

5. The polypeptide of claim 1, further comprising:
  a. a six repeat histidine tag attached to the N-terminus of the polypeptide; and
  b. a membrane carrier peptide attached to the C-terminus of the polypeptide.

6. The polypeptide of claim 1, comprising consecutive amino acids AQAGKEPGGSRAHSSHLKSKKGQSTSRH-KKLMFKTEGPDSD(glycine)DSDPG ETKFM-LKKHRSTSQGKKSKLHSSHARSGGPEKGAQA(glycine)AQAGKEPGGS RAHSSHLKSKKGQSTSRHKKLMFKTEGPDSD(glycine)DSDPGETKFMLKKHR STSQGKKSKLH-SSHARSGGPEKGAQA (SEQ ID NO:5), wherein each glycine may be present or absent.

7. The polypeptide of claim 6, further comprising a six repeat histidine tag attached to the N-terminus of the polypeptide.

8. The polypeptide of claim 6, further comprising a membrane carrier peptide attached to the C-terminus of the polypeptide.

9. The polypeptide of claim 8, wherein the membrane carrier peptide comprises amino acids having the sequence KKWKMRRNQFWVKVQRG (SEQ ID NO:8).

10. The polypeptide of claim 6, further comprising:
  a. a six repeat histidine tag attached to the N-terminus of the polypeptide; and
  b. a membrane carrier peptide attached to the C-terminus of the polypeptide.

11. The polypeptide of claim 1, comprising consecutive amino acids DSDPGETKFMLKKHRSTSQGKKSKLH-SSHARSGGPEKGAQA(glycine)AQAGK EPGGSRAH-SSHLKSKKGQSTSRHKKLMFKTEGPDSD(glycine)DS-DPGETKFM LKKHRSTSQGKKSKLHSSHARSGGPEKGAQA(glycine)AQAGKEPGGSRAHSS HLKSKKGQSTSRHKKLM-FKTEGPDSD (SEQ ID NO:6), wherein each glycine may be present or absent.

12. The polypeptide of claim 11, further comprising a six repeat histidine tag attached to the N-terminus of the polypeptide.

13. The polypeptide of claim 11, further comprising a membrane carrier peptide attached to the C-terminus of the polypeptide.

14. The polypeptide of claim 13, wherein the membrane carrier peptide comprises amino acids KKWKMRRNQF-WVKVQRG (SEQ ID NO:8).

15. The polypeptide of claim 11, further comprising:
  a. a six repeat histidine tag attached to the N-terminus of the polypeptide; and
  b. a membrane carrier peptide attached to the C-terminus of the polypeptide.

16. A pharmaceutical composition comprising the polypeptide of claim 1 and a pharmaceutically acceptable carrier for treating cancer.

* * * * *

SEQUENCE LISTING

```
<160> NUMBER OF SEQ ID NOS: 9

<210> SEQ ID NO 1
<211> LENGTH: 41
<212> TYPE: PRT
<213> ORGANISM: Artificial Sequence
<220> FEATURE:
<223> OTHER INFORMATION: Polypeptide based on human p53

<400> SEQUENCE: 1

Ala Gln Ala Gly Lys Glu Pro Gly Gly Ser Arg Ala His Ser Ser His
1               5                   10                  15

Leu Lys Ser Lys Lys Gly Gln Ser Thr Ser Arg His Lys Lys Leu Met
            20                  25                  30
```

```
Phe Lys Thr Glu Gly Pro Asp Ser Asp
        35                  40
```

```
<210> SEQ ID NO 2
<211> LENGTH: 41
<212> TYPE: PRT
<213> ORGANISM: Artificial Sequence
<220> FEATURE:
<223> OTHER INFORMATION: Polypeptide based on human p53

<400> SEQUENCE: 2
```

```
Asp Ser Asp Pro Gly Glu Thr Lys Phe Met Leu Lys Lys His Arg Ser
1               5                   10                  15

Thr Ser Gln Gly Lys Lys Ser Lys Leu His Ser Ser His Ala Arg Ser
            20                  25                  30

Gly Gly Pro Glu Lys Gly Ala Gln Ala
        35                  40
```

```
<210> SEQ ID NO 3
<211> LENGTH: 83
<212> TYPE: PRT
<213> ORGANISM: Artificial Sequence
<220> FEATURE:
<223> OTHER INFORMATION: Palindromic polypeptide based on human p53
<220> FEATURE:
<221> NAME/KEY: MISC_FEATURE
<222> LOCATION: (42)..(42)
<223> OTHER INFORMATION: Xaa = Gly or absent

<400> SEQUENCE: 3
```

```
Ala Gln Ala Gly Lys Glu Pro Gly Gly Ser Arg Ala His Ser Ser His
1               5                   10                  15

Leu Lys Ser Lys Lys Gly Gln Ser Thr Ser Arg His Lys Lys Leu Met
            20                  25                  30

Phe Lys Thr Glu Gly Pro Asp Ser Asp Xaa Asp Ser Asp Pro Gly Glu
        35                  40                  45

Thr Lys Phe Met Leu Lys Lys His Arg Ser Thr Ser Gln Gly Lys Lys
    50                  55                  60

Ser Lys Leu His Ser Ser His Ala Arg Ser Gly Gly Pro Glu Lys Gly
65                  70                  75                  80

Ala Gln Ala
```

```
<210> SEQ ID NO 4
<211> LENGTH: 83
<212> TYPE: PRT
<213> ORGANISM: Artificial Sequence
<220> FEATURE:
<223> OTHER INFORMATION: Palindromic polypeptide based on human p53
<220> FEATURE:
<221> NAME/KEY: MISC_FEATURE
<222> LOCATION: (42)..(42)
<223> OTHER INFORMATION: Xaa = Gly or absent

<400> SEQUENCE: 4
```

```
Asp Ser Asp Pro Gly Glu Thr Lys Phe Met Leu Lys Lys His Arg Ser
1               5                   10                  15

Thr Ser Gln Gly Lys Lys Ser Lys Leu His Ser Ser His Ala Arg Ser
            20                  25                  30

Gly Gly Pro Glu Lys Gly Ala Gln Ala Xaa Ala Gln Ala Gly Lys Glu
        35                  40                  45

Pro Gly Gly Ser Arg Ala His Ser Ser His Leu Lys Ser Lys Lys Gly
    50                  55                  60
```

Gln Ser Thr Ser Arg His Lys Lys Leu Met Phe Lys Thr Glu Gly Pro
65                  70                  75                  80

Asp Ser Asp

<210> SEQ ID NO 5
<211> LENGTH: 167
<212> TYPE: PRT
<213> ORGANISM: Artificial Sequence
<220> FEATURE:
<223> OTHER INFORMATION: Palindromic polypeptide based on human p53
<220> FEATURE:
<221> NAME/KEY: MISC_FEATURE
<222> LOCATION: (42)..(42)
<223> OTHER INFORMATION: Xaa = Gly or absent
<220> FEATURE:
<221> NAME/KEY: MISC_FEATURE
<222> LOCATION: (84)..(84)
<223> OTHER INFORMATION: Xaa = Gly or absent
<220> FEATURE:
<221> NAME/KEY: MISC_FEATURE
<222> LOCATION: (126)..(126)
<223> OTHER INFORMATION: Xaa = Gly or absent

<400> SEQUENCE: 5

Ala Gln Ala Gly Lys Glu Pro Gly Gly Ser Arg Ala His Ser His
1               5                   10                  15

Leu Lys Ser Lys Lys Gly Gln Ser Thr Ser Arg His Lys Lys Leu Met
            20                  25                  30

Phe Lys Thr Glu Gly Pro Asp Ser Asp Xaa Asp Ser Asp Pro Gly Glu
            35                  40                  45

Thr Lys Phe Met Leu Lys Lys His Arg Ser Thr Ser Gln Gly Lys Lys
        50                  55                  60

Ser Lys Leu His Ser Ser His Ala Arg Ser Gly Gly Pro Glu Lys Gly
65                  70                  75                  80

Ala Gln Ala Xaa Ala Gln Ala Gly Lys Glu Pro Gly Gly Ser Arg Ala
                85                  90                  95

His Ser Ser His Leu Lys Ser Lys Lys Gly Gln Ser Thr Ser Arg His
            100                 105                 110

Lys Lys Leu Met Phe Lys Thr Glu Gly Pro Asp Ser Asp Xaa Asp Ser
            115                 120                 125

Asp Pro Gly Glu Thr Lys Phe Met Leu Lys Lys His Arg Ser Thr Ser
        130                 135                 140

Gln Gly Lys Lys Ser Lys Leu His Ser Ser His Ala Arg Ser Gly Gly
145                 150                 155                 160

Pro Glu Lys Gly Ala Gln Ala
                165

<210> SEQ ID NO 6
<211> LENGTH: 167
<212> TYPE: PRT
<213> ORGANISM: Artificial Sequence
<220> FEATURE:
<223> OTHER INFORMATION: Palindromic polypeptide based on human p53
<220> FEATURE:
<221> NAME/KEY: MISC_FEATURE
<222> LOCATION: (42)..(42)
<223> OTHER INFORMATION: Xaa = Gly or absent
<220> FEATURE:
<221> NAME/KEY: MISC_FEATURE
<222> LOCATION: (84)..(84)
<223> OTHER INFORMATION: Xaa = Gly or absent
<220> FEATURE:
<221> NAME/KEY: MISC_FEATURE
<222> LOCATION: (126)..(126)

<223> OTHER INFORMATION: Xaa = Gly or absent

<400> SEQUENCE: 6

```
Asp Ser Asp Pro Gly Glu Thr Lys Phe Met Leu Lys Lys His Arg Ser
1               5                   10                  15

Thr Ser Gln Gly Lys Lys Ser Lys Leu His Ser Ser His Ala Arg Ser
            20                  25                  30

Gly Gly Pro Glu Lys Gly Ala Gln Ala Xaa Ala Gln Ala Gly Lys Glu
        35                  40                  45

Pro Gly Gly Ser Arg Ala His Ser Ser His Leu Lys Ser Lys Lys Gly
    50                  55                  60

Gln Ser Thr Ser Arg His Lys Lys Leu Met Phe Lys Thr Glu Gly Pro
65                  70                  75                  80

Asp Ser Asp Xaa Asp Ser Asp Pro Gly Glu Thr Lys Phe Met Leu Lys
                85                  90                  95

Lys His Arg Ser Thr Ser Gln Gly Lys Lys Ser Lys Leu His Ser Ser
                100                 105                 110

His Ala Arg Ser Gly Gly Pro Glu Lys Gly Ala Gln Ala Xaa Ala Gln
            115                 120                 125

Ala Gly Lys Glu Pro Gly Gly Ser Arg Ala His Ser Ser His Leu Lys
        130                 135                 140

Ser Lys Lys Gly Gln Ser Thr Ser Arg His Lys Lys Leu Met Phe Lys
145                 150                 155                 160

Thr Glu Gly Pro Asp Ser Asp
                165
```

<210> SEQ ID NO 7
<211> LENGTH: 164
<212> TYPE: PRT
<213> ORGANISM: Artificial Sequence
<220> FEATURE:
<223> OTHER INFORMATION: Palindromic polypeptide based on human p53

<400> SEQUENCE: 7

```
Ala Gln Ala Gly Lys Glu Pro Gly Gly Ser Arg Ala His Ser Ser His
1               5                   10                  15

Leu Lys Ser Lys Lys Gly Gln Ser Thr Ser Arg His Lys Lys Leu Met
            20                  25                  30

Phe Lys Thr Glu Gly Pro Asp Ser Asp Asp Ser Asp Pro Gly Glu Thr
        35                  40                  45

Lys Phe Met Leu Lys Lys His Arg Ser Thr Ser Gln Gly Lys Lys Ser
    50                  55                  60

Lys Leu His Ser Ser His Ala Arg Ser Gly Gly Pro Glu Lys Gly Ala
65                  70                  75                  80

Gln Ala Ala Gln Ala Gly Lys Glu Pro Gly Gly Ser Arg Ala His Ser
            85                  90                  95

Ser His Leu Lys Ser Lys Lys Gly Gln Ser Thr Ser Arg His Lys Lys
                100                 105                 110

Leu Met Phe Lys Thr Glu Gly Pro Asp Ser Asp Asp Ser Asp Pro Gly
            115                 120                 125

Glu Thr Lys Phe Met Leu Lys Lys His Arg Ser Thr Ser Gln Gly Lys
        130                 135                 140

Lys Ser Lys Leu His Ser Ser His Ala Arg Ser Gly Gly Pro Glu Lys
145                 150                 155                 160

Gly Ala Gln Ala
```

```
<210> SEQ ID NO 8
<211> LENGTH: 17
<212> TYPE: PRT
<213> ORGANISM: Artificial Sequence
<220> FEATURE:
<223> OTHER INFORMATION: Membrane carrier peptide derived from
      Antennaepedia

<400> SEQUENCE: 8

Lys Lys Trp Lys Met Arg Arg Asn Gln Phe Trp Val Lys Val Gln Arg
1               5                   10                  15

Gly

<210> SEQ ID NO 9
<211> LENGTH: 6
<212> TYPE: DNA
<213> ORGANISM: Artificial Sequence
<220> FEATURE:
<223> OTHER INFORMATION: Restriction enzyme site derived from human p53

<400> SEQUENCE: 9 ggccgg                                                           6
```